US012622666B2

(12) United States Patent
Takahashi et al.

(10) Patent No.: US 12,622,666 B2
(45) Date of Patent: May 12, 2026

(54) CALIBRATION PHANTOM

(71) Applicant: FUJIFILM Corporation, Tokyo (JP)

(72) Inventors: Isao Takahashi, Tokyo (JP); Shinichi Kojima, Tokyo (JP); Kazuma Yokoi, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 166 days.

(21) Appl. No.: 18/815,014

(22) Filed: Aug. 26, 2024

(65) Prior Publication Data

US 2025/0090129 A1     Mar. 20, 2025

(30) Foreign Application Priority Data

Sep. 20, 2023   (JP) ................................. 2023-151793

(51) Int. Cl.
*A61B 6/58*          (2024.01)
(52) U.S. Cl.
CPC .................................... *A61B 6/583* (2013.01)
(58) Field of Classification Search
CPC ...................................................... A61B 6/583
See application file for complete search history.

(56) References Cited

U.S. PATENT DOCUMENTS

2023/0200757 A1 *   6/2023   Yokoi ................... A61B 6/032
378/4

FOREIGN PATENT DOCUMENTS

JP          2013-146480 A      8/2013

OTHER PUBLICATIONS

Lee et al., "Calculation of Stopping-Power Ratio from Multiple CT Nos. Using Photon-Counting CT System: Two- and Three-Parameter-Fitting Method", Sensors vol. 21, 1215. (Year: 2021).*

* cited by examiner

*Primary Examiner* — Kiho Kim
(74) *Attorney, Agent, or Firm* — Paul Teng

(57)          ABSTRACT

A calibration phantom is configured to be difficult to deform and easy to handle. The calibration phantom can be used in a case of acquiring calibration data of a photon-counting type detector that outputs an electrical signal corresponding to photon energy of an incident X-ray. The calibration phantom includes first base substances and a second base substance which are known substances, the second base substance having an atomic number larger than an atomic number of the first base substances and being sandwiched between the first base substances.

3 Claims, 4 Drawing Sheets

CALIBRATION PHANTOM

CROSS REFERENCE TO RELATED APPLICATION

The present application claims priority from Japanese Patent Application JP 2023-151793 filed on Sep. 20, 2023, the content of which is hereby incorporated by reference into this application.

BACKGROUND OF THE INVENTION

1. Field of the Invention

The present invention relates to an X-ray computed tomography (CT) apparatus comprising a photon-counting type detector, and relates to a calibration phantom used for calibration of the photon-counting type detector.

2. Description of the Related Art

The X-ray CT apparatus is an apparatus that generates a tomographic image of a subject by using a plurality of projection data acquired by executing irradiation of the subject with X-rays and detection of the X-rays transmitted through the subject at a plurality of projection angles. The generated tomographic image is used as a medical image for diagnosing the subject.

In a photon-counting CT apparatus using the photon-counting type detector for the X-rays detection, a tomographic image decomposed into substances of different compositions, for example, tomographic images decomposed into an iodine contrast agent used in angiography and a soft tissue are obtained as medical images. In order to obtain the tomographic images decomposed into the substances, it is necessary to acquire, in advance, a relationship between output and photon energy in a case in which a phantom composed of a combination of a plurality of base substances, which are substances of which a composition and a thickness are known, is measured with the photon-counting type detector, as calibration data for each detection element.

JP2013-146480A discloses that a two-dimensional map of acrylic thickness-iodine thickness is obtained as calibration data using a stepped phantom consisting of acrylic and iodine.

SUMMARY OF THE INVENTION

However, JP2013-146480A lacks consideration for handling the phantom. In the phantom composed of the combination of the plurality of base substances, a thickness of a base substance having a relatively large atomic number may be made extremely thin, for example, about 0.1 mm. The base substance having a thickness of about 0.1 mm is easily deformed, and in calibration data acquired using the phantom composed of the deformed base substance, an accuracy of discriminating the substance is lowered.

An object of the present invention is to provide a calibration phantom that is difficult to be deformed and is easy to handle.

In order to achieve the above object, according to the present invention, there is provided a calibration phantom used in a case of acquiring calibration data of a photon-counting type detector that outputs an electrical signal corresponding to photon energy of an incident X-ray, the calibration phantom comprising: first base substances and a second base substance which are known substances, the second base substance having an atomic number larger than an atomic number of the first base substances and being sandwiched between the first base substances.

According to the present invention, it is possible to provide a calibration phantom that is difficult to be deformed and is easy to handle.

DESCRIPTION OF THE PREFERRED EMBODIMENTS

Figure 1:
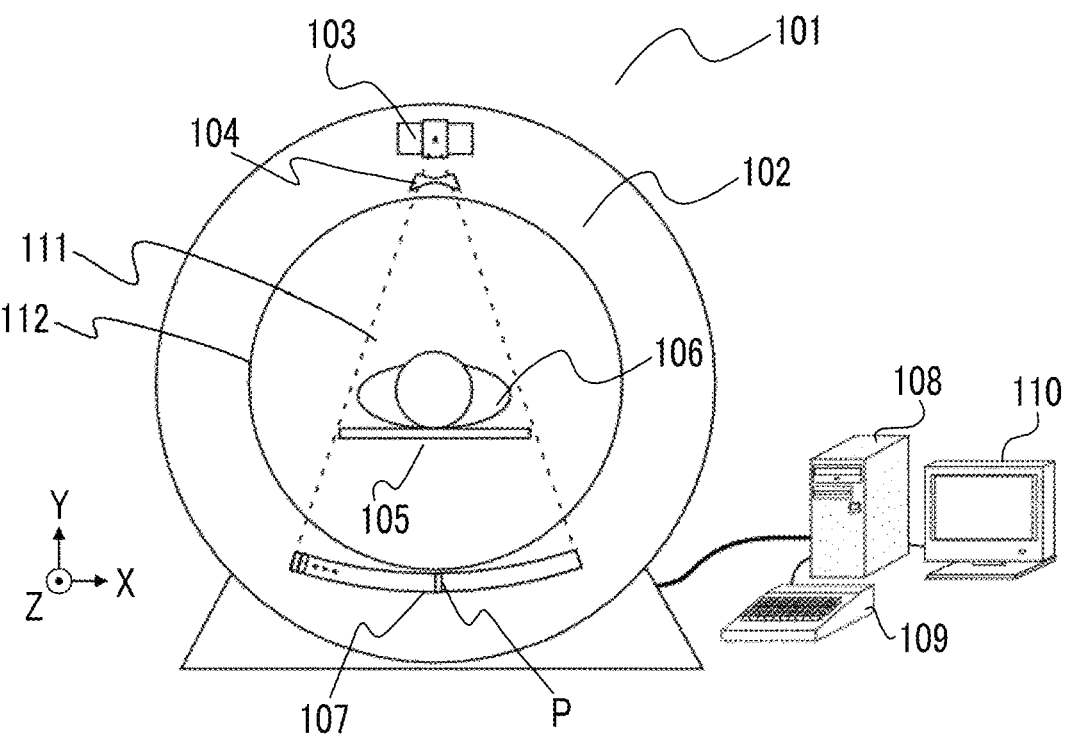
FIG. 1 is a diagram showing an overall configuration of a photon-counting CT apparatus.

Hereinafter, an embodiment of a calibration phantom according to the present invention will be described with reference to the drawings. The calibration phantom according to the embodiment of the present invention is used in a photon-counting CT apparatus comprising a photon-counting type detector. In the following description and the accompanying drawings, components having the same functional configuration are designated by the same reference numerals, and duplicate description thereof will be omitted.

Example 1

FIG. 1 shows an overall configuration diagram of a photon-counting CT apparatus 101. A horizontal direction of a paper surface is defined as an X axis, a vertical direction is defined as a Y axis, and a direction orthogonal to an XY plane is defined as a Z axis. The photon-counting CT apparatus 101 comprises a gantry 102, an X-ray tube 103, a bow tie filter 104, an examination table 105, a detector panel 107, a computing device 108, an input device 109, and a display device 110.

A subject 106 is placed on the examination table 105 and is disposed in an opening portion 112 provided in the gantry 102. X-rays 111 radiated from the X-ray tube 103 is emitted to the subject 106 via the bow tie filter 104, are transmitted through the subject 106, and are then detected by the detector panel 107. The X-rays are formed into a beam shape suitable for a size of the subject 106 by passing through the bow tie filter 104. The X-ray tube 103 and the detector panel 107 are attached to the gantry 102 so as to be disposed to face each other with the subject 106 interposed therebetween, and are rotated around the subject 106 by a rotation drive unit of the gantry 102. The X-ray irradiation from the X-ray tube 103 and the X-ray measurement by the detector panel 107 are repeated while both the X-ray tube 103 and the detector panel 107 are rotated, thereby acquiring projection data at various projection angles.

The acquired projection data is subjected to image reconstruction processing by the computing device 108 to generate a tomographic image of the subject 106, and the tomographic image is displayed on the display device 110 as a medical image. In addition, in a case in which the projection data is acquired while the examination table 105 on which the subject 106 is placed and the gantry 102 are relatively moved in a Z axis direction, a volume image of the subject 106 is generated. An amount of X-rays emitted from the X-ray tube 103, a rotation speed of the gantry 102, and a relative movement speed between the gantry 102 and the examination table 105 are set based on scan conditions input by an operator via the input device 109. In addition, the computing device 108 has the same hardware configuration as a general computer device, and comprises a central processing unit (CPU), a memory, a hard disk drive (HDD), and the like, and performs correction processing on the projection data and the like, and controls each unit.

The detector panel 107 has a configuration in which a plurality of detection elements P are disposed in an arc shape centered on an X-ray focal point of the X-ray tube 103. In a case in which the detection element P is a photon-counting type detector, incident X-ray photons are individually counted, and the energy of the X-ray photons is measured.

In the photon-counting CT apparatus 101 comprising the photon-counting type detector, a photon energy spectrum related to the projection data of the subject 106 can be acquired, so that it is possible to generate medical images decomposed into substances of different compositions or medical images divided into a plurality of energy components. In order to obtain the medical images decomposed into the substances of different compositions, it is necessary to acquire calibration data of the photon-counting type detector in advance.

Figure 2:
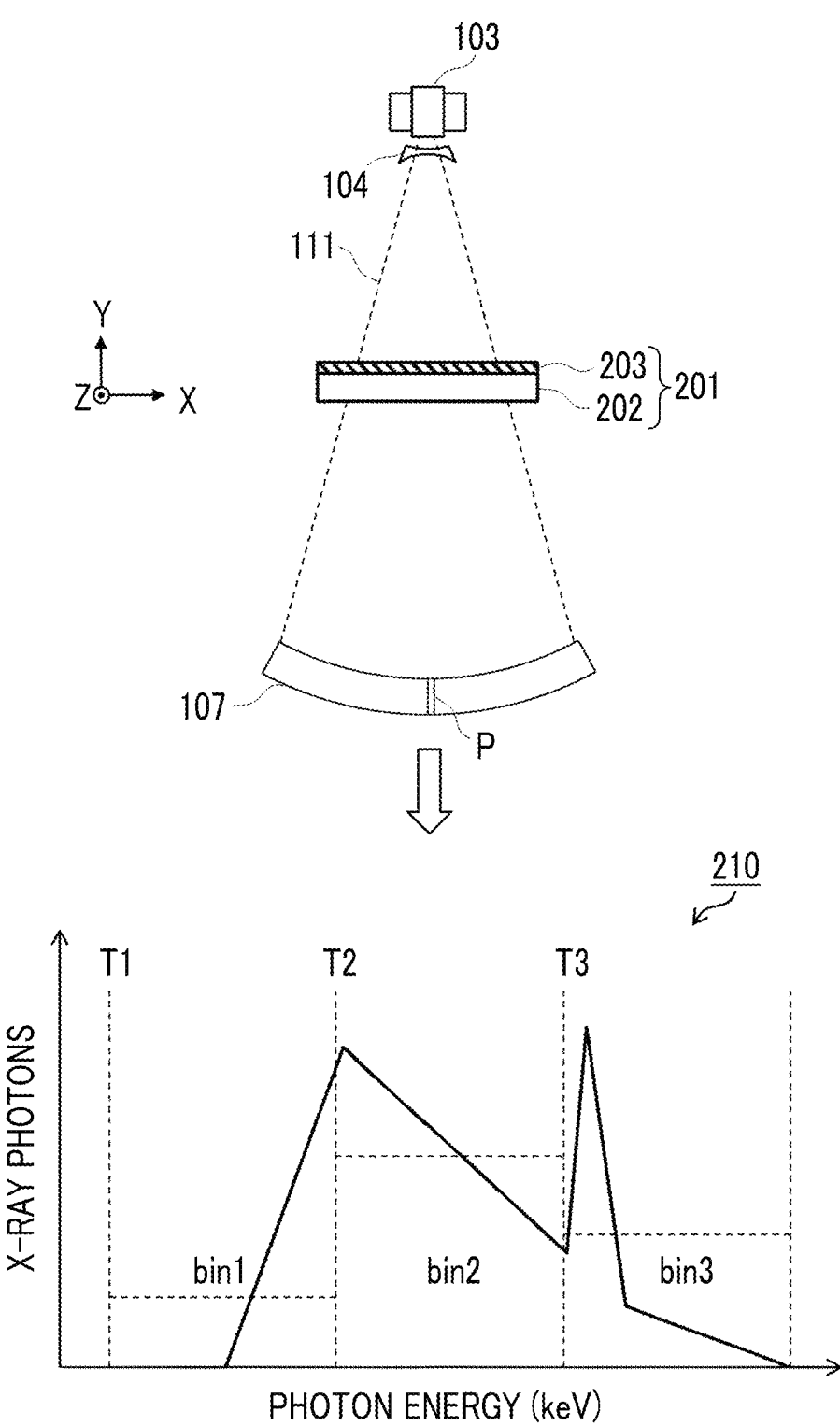
FIG. 2 is a diagram describing calibration data of a photon-counting type detector.

The calibration data of the photon-counting type detector will be described with reference to FIG. 2. For the acquisition of the calibration data of the photon-counting type detector, a calibration phantom 201 composed of a plurality of base substances of which a composition and a thickness are known is used. That is, a photon energy spectrum 210, which is the number of X-ray photons for each photon energy illustrated in a lower part of FIG. 2, is acquired in advance by counting the X-rays transmitted through the calibration phantom 201 with the detection element P of the photon-counting type detector. FIG. 2 shows the number of X-ray photons counted by being divided into three energy bins bin1, bin2, and bin3 of T1 to T2, T2 to T3, and T3 to the end. The calibration data is a group of photon energy spectra 210 acquired using a plurality of calibration phantoms 201 each having different thicknesses of the base substances, and is compared with a photon energy spectrum related to the projection data of the subject 106. Then, the subject 106 is decomposed into a plurality of base substances based on the thicknesses of the base substances of the calibration phantom 201 used for the acquisition of the photon energy spectrum 210 similar to the photon energy spectrum of the subject 106 from the calibration data.

The calibration phantom 201 is composed of, for example, a first base substance 202 corresponding to a soft tissue of the subject 106 and a second base substance 203 corresponding to an iodine contrast agent used in angiography. Specifically, the first base substance 202 corresponding to the soft tissue is an acrylic plate, and the second base substance 203 corresponding to the iodine contrast agent is a tin plate. The first base substance 202 may be a substance other than acrylic as long as it is a substance corresponding to water or a soft tissue. In addition, the second base substance 203 may be silver other than tin as long as it is a substance corresponding to an iodine contrast agent, or may be aluminum or titanium corresponding to a bone of the subject 106, or other metals such as rhodium, palladium, lead, gold, platinum, tungsten, or alloys thereof. That is, the second base substance 203 has an atomic number larger than an atomic number of the first base substance 202.

Incidentally, a thickness of the tin plate corresponding to the iodine contrast agent flowing in a blood vessel may be, for example, about 0.1 mm based on a concentration of the iodine contrast agent in blood. The tin plate having a thickness of about 0.1 mm is easily deformed, and the number of X-ray photons transmitted through the calibration phantom 201 changes due to the deformation of the tin plate, so that an error included in the acquired calibration data is increased. That is, an accuracy of discriminating the substance is lowered due to the deformation of the calibration phantom 201. Therefore, in Example 1, the calibration phantom 201 is configured such that the deformation of the base substance is suppressed.

Figure 3:
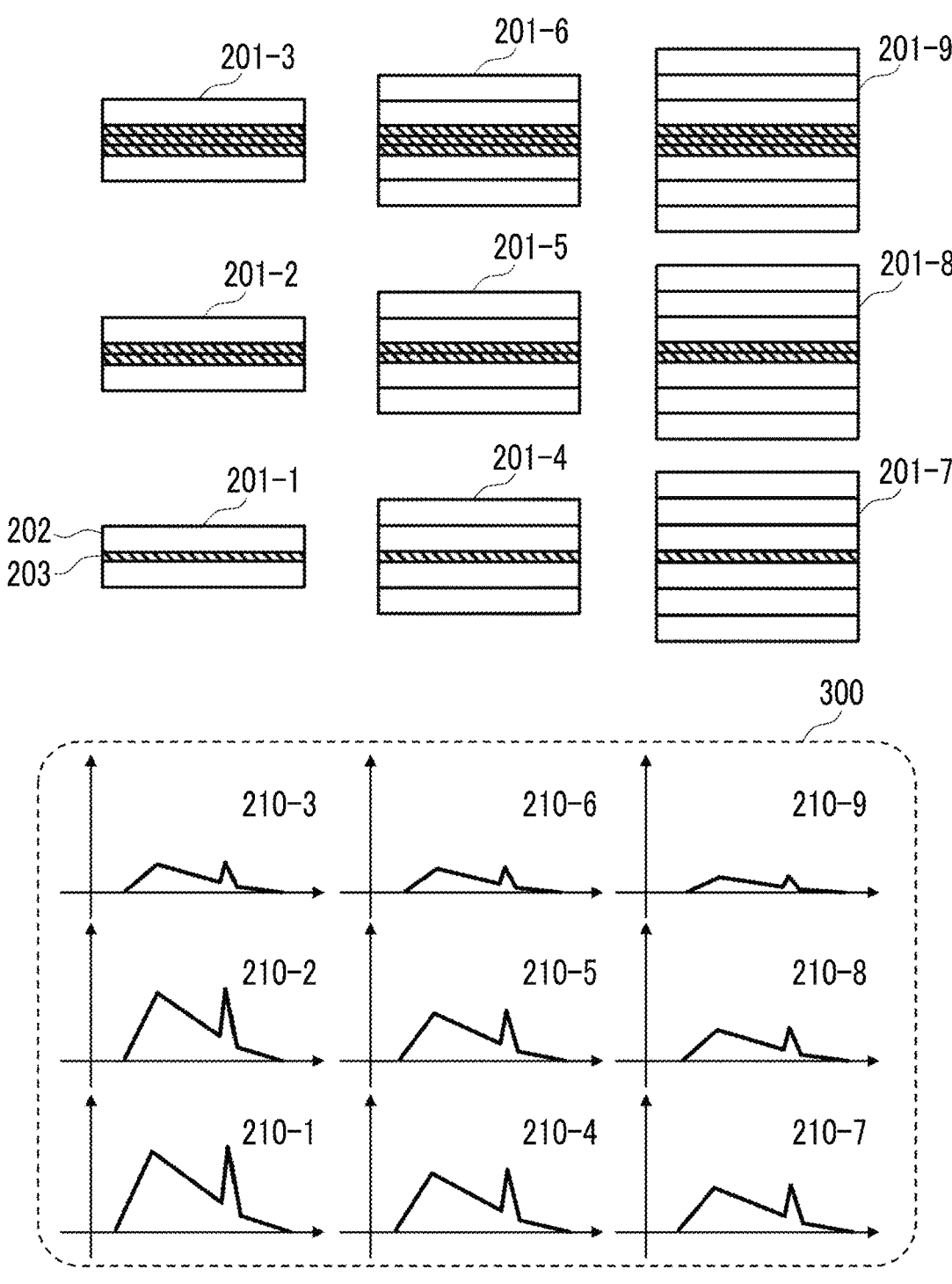
FIG. 3 is a diagram showing a configuration example of a calibration phantom and an example of calibration data acquired using the calibration phantom.

The calibration phantom 201 of Example 1 will be described with reference to FIG. 3. FIG. 3 illustrates nine types of calibration phantoms 201-1 to 201-9 composed of first base substances 202 and a second base substance 203. Each of the nine types of calibration phantoms 201-1 to 201-9 is configured such that the second base substance 203 is sandwiched between the first base substances 202. With such a configuration, even in a case in which the second base substance 203 is a flat plate having a thickness of 1 mm or less and is easily deformed, the second base substance 203 is constrained by the first base substances 202, so that the deformation of the second base substance 203 is suppressed, and the error included in the acquired calibration data can be reduced.

Since the first base substance 202 has an atomic number smaller than an atomic number of the second base substance 203, the first base substance 202 is a flat plate having a larger thickness than a thickness of the second base substance 203 and is difficult to be deformed. For example, the first base substance 202 is an acrylic plate having a thickness of 10 mm, and the second base substance 203 is a tin plate having a thickness of 0.1 mm.

More specifically, the calibration phantom 201-1 has a configuration in which one tin plate having a thickness of 0.1 mm is sandwiched between two acrylic plates having a thickness of 10 mm. In addition, the calibration phantom 201-2 has a configuration in which two tin plates having a thickness of 0.1 mm are sandwiched between two acrylic plates having a thickness of 10 mm, and the calibration phantom 201-3 has a configuration in which three tin plates having a thickness of 0.1 mm are sandwiched between two acrylic plates having a thickness of 10 mm.

Similarly, the calibration phantom 201-4 has a configuration in which one tin plate having a thickness of 0.1 mm is sandwiched between four acrylic plates having a thickness of 10 mm, the calibration phantom 201-5 has a configuration in which two tin plates having a thickness of 0.1 mm are sandwiched between four acrylic plates having a thickness of 10 mm, and the calibration phantom 201-6 has a configuration in which three tin plates having a thickness of 0.1 mm are sandwiched between four acrylic plates having a thickness of 10 mm. Furthermore, the calibration phantom 201-7 has a configuration in which one tin plate having a thickness of 0.1 mm is sandwiched between six acrylic plates having a thickness of 10 mm, the calibration phantom 201-8 has a configuration in which two tin plates having a thickness of 0.1 mm are sandwiched between six acrylic plates having a thickness of 10 mm, and the calibration phantom 201-9 has a configuration in which three tin plates having a thickness of 0.1 mm are sandwiched between six acrylic plates having a thickness of 10 mm.

A lower part of FIG. 3 illustrates calibration data 300 acquired using the calibration phantoms 201-1 to 201-9. That is, photon energy spectra 210-1 to 210-9 acquired using the calibration phantoms 201-1 to 201-9 are the calibration data 300. The calibration phantom 201-1 and the photon energy spectrum 210-1 correspond to each other, the calibration phantom 201-2 and the photon energy spectrum 210-2 correspond to each other, . . . , and the calibration phantom 201-9 and the photon energy spectrum 210-9 correspond to each other. The calibration data 300 may include a photon energy spectrum acquired without using the calibration phantom 201, that is, a photon energy spectrum of X-rays transmitted through air.

The calibration phantoms 201-1 to 201-9 in which upper and lower thicknesses of the first base substances 202 between which the second base substance 203 is sandwiched, as illustrated in FIG. 3, are equal have an advantage in that the calibration phantoms are difficult to be deformed. Note that the calibration phantom 201 is not limited to FIG. 3, and the upper and lower thicknesses of the first base substances 202 may be different. That is, in a case in which the thickness of the first base substance 202 through which the X-rays are transmitted is known, the acquired photon energy spectrum 210 can be used as the calibration data 300.

Figure 4:
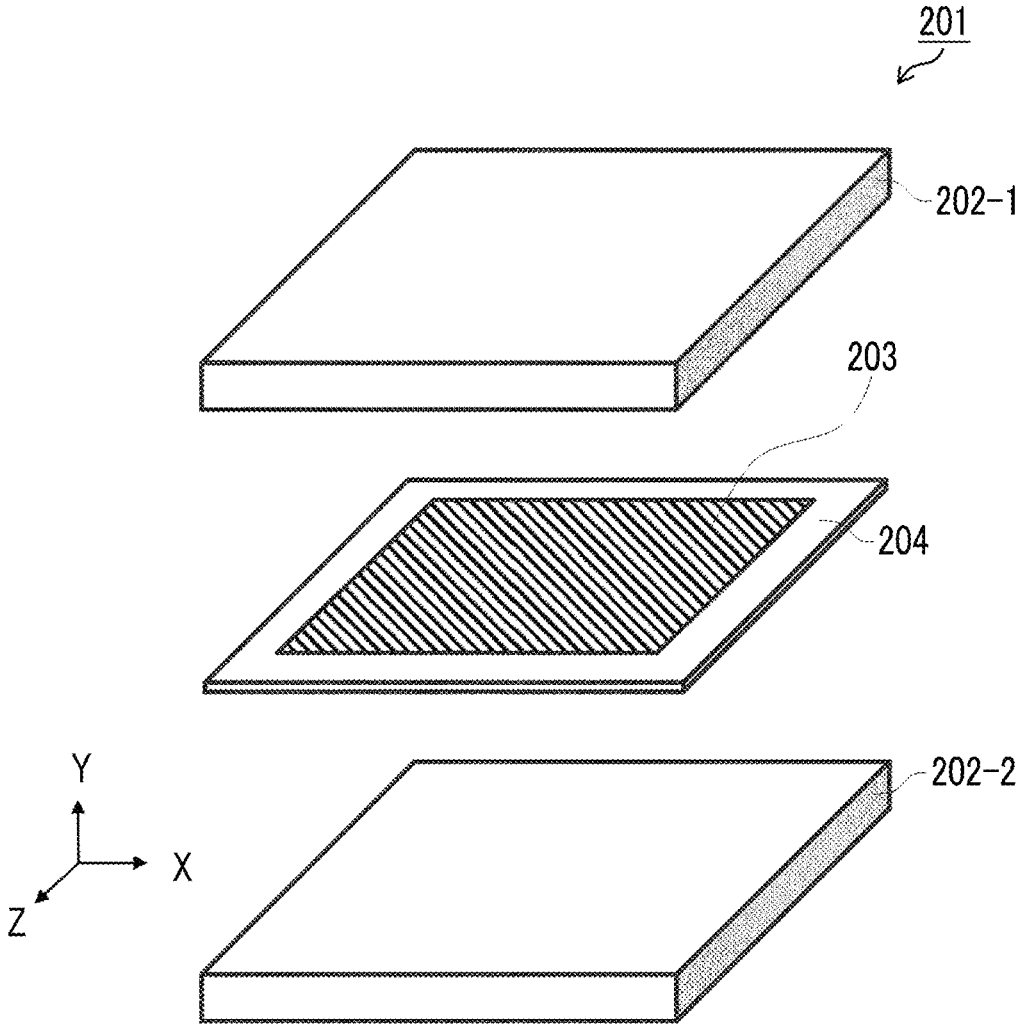
FIG. 4 is a diagram showing another configuration example of the calibration phantom.

Another example of the calibration phantom 201 will be described with reference to FIG. 4. FIG. 4 is a perspective view of the calibration phantom 201 in a state before the second base substance 203 is sandwiched between the first base substances 202. The calibration phantom 201 illustrated in FIG. 4 is composed of two first base substances 202-1 and 202-2, a second base substance 203, and an outer frame portion 204. The outer frame portion 204 has a frame shape, and the second base substance 203 is fitted into the outer frame portion 204. That is, a side surface of the second base substance 203 is covered with the outer frame portion 204. A thickness of the outer frame portion 204 is equal to or greater than the thickness of the second base substance 203. The first base substance 202-1 and the first base substance 202-2 are disposed on an upper side and a lower side of the outer frame portion 204 into which the second base substance 203 is fitted, and the second base substance 203 and the outer frame portion 204 are sandwiched between the first base substance 202-1 and the first base substance 202-2. The outer frame portion 204 may be formed from the first base substance 202.

In the calibration phantom 201 configured as shown in FIG. 4, since the second base substance 203 is not exposed, even in a case in which the second base substance 203 is extremely thin, the deformation of the second base substance 203 is further suppressed, and the error included in the acquired calibration data can be further reduced.

An example of the present invention has been described above. It should be noted that the present invention is not limited to the above-described example, and the components can be modified and embodied without departing from the gist of the invention. In addition, a plurality of components disclosed in the above-described example may be combined as appropriate. Further, some components may be deleted from all the components described in the above-described example.

EXPLANATION OF REFERENCES

101: photon-counting CT apparatus
102: gantry
103: X-ray tube
104: bow tie filter
105: examination table
106: subject
107: detector panel
108: computing device
109: input device
110: display device
111: X-ray
112: opening portion
201: calibration phantom
202: first base substance
203: second base substance
204: outer frame portion
210: photon energy spectrum
300: calibration data

What is claimed is:

1. A calibration phantom used in a case of acquiring calibration data of a photon-counting type detector that outputs an electrical signal corresponding to photon energy of an incident X-ray, the calibration phantom comprising:
   first base substances and a second base substance which are known substances, the second base substance having an atomic number larger than an atomic number of the first base substances and being sandwiched between the first base substances.

2. The calibration phantom according to claim 1, wherein upper and lower thicknesses of the first base substances between which the second base substance is sandwiched are equal.

3. The calibration phantom according to claim 1, wherein the second base substance is sandwiched between the first base substances and has a covered side surface.

* * * * *